US007902249B2

(12) United States Patent
Luu et al.

(10) Patent No.: US 7,902,249 B2
(45) Date of Patent: *Mar. 8, 2011

(54) INDOLE DERIVATIVES SUBSTITUTED WITH LONG-CHAIN ALCOHOLS AND MEDICAMENTS CONTAINING THEM

(75) Inventors: Bang Luu, Strasbourg (FR); Djalil Coowar, Strasbourg (FR); Masashi Yamada, Tokyo (JP); Yukie Suma, Tokyo (JP); Hiroto Suzuki, Tokyo (JP)

(73) Assignee: Meiji Dairies Corporation, Tokyo (JP)

( * ) Notice: Subject to any disclaimer, the term of this patent is extended or adjusted under 35 U.S.C. 154(b) by 357 days.

This patent is subject to a terminal disclaimer.

(21) Appl. No.: 12/132,345

(22) Filed: Jun. 3, 2008

(65) Prior Publication Data

US 2008/0234357 A1 Sep. 25, 2008

Related U.S. Application Data

(63) Continuation of application No. 10/504,484, filed as application No. PCT/JP02/01192 on Feb. 13, 2002, now Pat. No. 7,407,983.

(51) Int. Cl.
A61K 31/404 (2006.01)
C07D 209/04 (2006.01)

(52) U.S. Cl. ......... 514/415; 548/469; 548/509; 514/412

(58) Field of Classification Search ................. 548/469, 548/509; 514/412, 415
See application file for complete search history.

(56) References Cited

U.S. PATENT DOCUMENTS

| | | | |
|---|---|---|---|
| 3,197,479 A | 7/1965 | Johnson | |
| 5,447,959 A | 9/1995 | Borg | |
| 5,552,534 A | 9/1996 | Hirschmann et al. | |
| 5,665,725 A * | 9/1997 | Moltzen et al. | 514/278 |
| 5,776,967 A | 7/1998 | Kreft et al. | |
| 5,811,512 A | 9/1998 | Hirschmann et al. | |
| 5,990,094 A | 11/1999 | Cole et al. | |
| 6,194,217 B1 * | 2/2001 | Matson | 436/63 |
| 6,197,963 B1 | 3/2001 | Hirschmann et al. | |
| 6,207,677 B1 * | 3/2001 | Moltzen et al. | 514/304 |
| 7,307,098 B2 * | 12/2007 | Luu et al. | 514/415 |
| 7,407,983 B2 * | 8/2008 | Luu et al. | 514/415 |

FOREIGN PATENT DOCUMENTS

| | | |
|---|---|---|
| EP | 0 396 124 | 11/1990 |
| EP | 0 548 813 | 6/1993 |
| FR | 2 499 987 | 8/1982 |
| GB | 778 823 | 7/1957 |
| JP | 4-502167 | 4/1992 |
| WO | 90 14084 | 11/1990 |
| WO | WO 92 22554 | 12/1992 |
| WO | 96 20191 | 7/1996 |

OTHER PUBLICATIONS

Moltzen et al (1993): STN International CAPLUS database, (Columbus, Ohio), Accession number: 1993:517118.*

Matsui et al (1991): STN International CAPLUS database, (Columbus, Ohio), Accession number: 1991:143418.*
Hirschmann et al. (1998): STN International CAPLUS database, (Columbus, Ohio), Accession number: 1998:618388.
Moltzen, et al. (1993): STN International CAPLUS database, (Columbus, Ohio), Accession number: 1993:517118.
Koo, et al., Database Crossfire Beilstein 'Online! Beilstein Institut zur Foerderung der Chemischen Wissenschaften, Frankfurt am Main, DE; Database ascession No. 143517, J. Org. Chem., vol. 24, pp. 179-183, 1959.
V. Erspamer, R. Ferrini, A. Glaesser: "A note on the oxidative deamination of isomers of 5-hydroxytryptamine and other indolealkylamines" J. Pharm. Pharmacol., vol. 12, No. 5-9, pp. 761-764, 1960.
C.A. Demerson, L.G. Humber, A.H.Philipp, "Etodolic Acid and related Compounds. Chemistry and Antiinflammatory Actions of Some Potent Di- and Trisubstituted 1,3,4,9-Tetrahydropyrano[3,4-b]indole-1-acetic Acids", J.Med.Chem., vol. 19, No. 3, pp. 391-395, schemes 1;2, example E, 1976.
L.G.Humber, C.A. Demerson, A.A. Asselin:"A novel class of potential antidepressants 1-aminoalky1-1,3,4,9-tetrahydropyrano[3,4-b]indoles" Eur.J.Med.Chem.Chim.Ther, vol. 10, No. 3, pp. 215-220, scheme 1-compound 1, p. 218, col. 1, 1975.
J. Manske, Database Crossfire Beilstein 'Online! Beilstein Institut zur Foerderung der Chemischen Wissenschaften, Frankfurt am Main, DE; Database accession no. 134161, J. Amer.Chem.Soc., Vol. 52, pp. 5029-5031, 1930. L.G.Humber, C.A. Demerson, A.A.Asselin: "A novel class of potential antidepressants 1-aminoalky1-1,3,4,9-tetrahydropyrano[3,4-b]indoles", Eur.J.Med.Chem.Chim.Ther., vol. 10, No. 3, pp. 215-220, scheme 1-compound 1, p. 218, col. 1, 1975.
J.Manske, Database Crossfire Beilstein, 'Online! Beilstein Institut zur Foererung der Chemischen Wissenschaften, Frankfurt am Main, DE; Database ascession No. 134161, J. Amer.Chem.Soc., vol. 52, pp. 5029, 5031, 1930.

(Continued)

Primary Examiner — Golam M Shameem
(74) Attorney, Agent, or Firm — Oblon, Spivak, McClelland, Maier & Neustadt, L.L.P.

(57) ABSTRACT

Provided is an indole long-chain alcohol, or a hydrate or an isomer thereof, represented by the following formula (I):

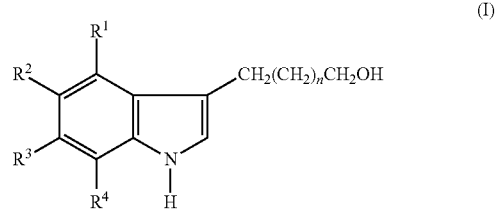

(I)

wherein $R^1$, $R^2$, $R^3$ and $R^4$ each independently represent a hydrogen atom, a methyl group, an acetyl group, or a hydroxyl group, and n represents a number from 0 to 20; and a medicinal composition comprising the same. The indole long-chain alcohol (I) exhibits an excellent nerve growth promoting effect, as well as potent antioxidative and anti-tumor effects, and is therefore useful as a prophylactic and/or therapeutic agent for cerebral diseases including dementia diseases, and malignant tumors including brain tumors.

18 Claims, 1 Drawing Sheet

OTHER PUBLICATIONS

I.I. Grandberg, T.P. Moskvina, Database Crossfire Beilstein 'Online! Beilstein Institut zur Foerderung der Chemischen Wissenschaften, Frankfurt am Main, DE; Database accession No. 1527688, 1527673, KHIM. vol. 74, No. 3, Columbus, OH US, 1970 & 1971.

A.J. Greenburg, R. Ketcham: "Determination of Urinary Indolic Metabolites", J. Pharm.Sci., vol. 67, No. 1, pp. 478-480, compounds IV & V, 1978.

C. Girlands-Junges, F. Keyling-Bilger, G. Schmitt, B. Luu, "Effect of Cyclohexenoic Long Chain Fatty Alsohols on Neurite Outgrowth. Study on Structure-Activity Relationship," Tetrahedron, vol. 54, pp. 7735-7748, cited in the application, pp. 7740-7742, figure 1, 1998.

* cited by examiner

INDOLE DERIVATIVES SUBSTITUTED WITH LONG-CHAIN ALCOHOLS AND MEDICAMENTS CONTAINING THEM

CROSS-REFERENCE TO RELATED APPLICATIONS

The present application is a continuation of U.S. patent application Ser. No. 10/504,484, filed on Aug. 12, 2004, which is a 35 U.S.C. §371 National Stage patent application of International patent application PCT/JP02/01192, filed on Feb. 13, 2002.

TECHNICAL FIELD

The present invention relates to an indole long-chain alcohol which exhibits an excellent nerve growth promoting effect and potent antioxidative and antitumor effects, and is therefore useful as a preventive and/or therapeutic agent for cerebral diseases typified by dementia or malignant tumors such as brain tumor; and a medicament containing the compound.

BACKGROUND ART

It is considered that the main lesion of Alzheimer's disease is degeneration and defluvium of cholinergic neurons. At present, a cholinesterase inhibitor or a muscalinic receptor agonist is used for the treatment of said disease. Such a medicament alleviates dementia symptomatically but cannot stop or retard the progress of the morbidity. There has also been made an attempt to treat Alzheimer's disease by administering a nerve growth factor (NGF) into the brain. NGF is expected to suppress degeneration and defluvium of neurons due to its neuron growth action, thereby terminating or retarding the progress of dementia. However, since NGF is a protein having a molecular weight of 12,000, it cannot pass through the blood-brain barrier and its administration route is confined only to intraventricular administration, which is not practical for the treatment of human beings. If there is such compound that exhibits an NGF-like action and has a molecular weight low enough to pass through the blood-brain barrier or such compound that can enhance the synthesis of NGF in the brain, it will be promising as a remedy effective for treating Alzheimer's dementia.

Based on such an idea, a substance which promotes and/or reinforces production of NGF has been searched, and it has been proved that long-chain aliphatic alcohols such as n-hexacosanol stimulate nerve growth factor in vitro and can pass through the blood-brain barrier in vivo (Japanese Patent Application Laid-Open No. 502167/1992).

DISCLOSURE OF THE INVENTION

Accordingly, an object of the present invention is to provide a medicament comprising a compound which is orally administrable, readily transferred into the brain, and permits extension of neurite in the brain or activates the synthesis and secretion of NGF.

The present inventors have synthesized a long-chain alcohol derivative having an indole skeleton and investigated its pharmacological action. As a result, it has been found that an indole long-chain alcohol represented by the formula (I) shown below exhibits an excellent nerve growth promoting effect and potential antioxidative and anti-tumor effects, and is therefore useful as a preventive and/or therapeutic drug for cerebral diseases such as dementia or malignant tumors such as cerebral tumor, to complete the present invention.

In one aspect of the present invention, there is thus provided an indole long-chain alcohol represented by the following formula (I):

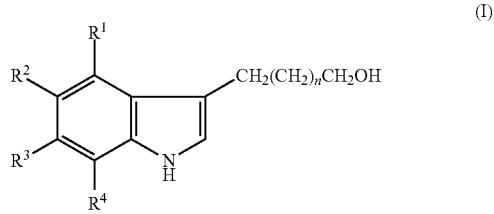

wherein $R^1$, $R^2$, $R^3$ and $R^4$ each independently represents a hydrogen atom, a methyl group, an acetyl group or a hydroxyl group and n stands for a number from 0 to 20.

In another aspect of the present invention, there is also provided a medicine comprising the compound of the formula (I) as an effective ingredient.

In a further aspect of the present invention, there is also provided a nerve growth promoting agent comprising the compound of the formula (I) as an effective ingredient.

In a still further aspect of the present invention, there is also provided a preventive and/or therapeutic drug for dementia and/or malignant tumors, which comprises the compound of the formula (I) as an effective ingredient.

In a still further aspect of the present invention, there is also provided a medical composition comprising the compound of the formula (I) together with a pharmaceutically acceptable carrier.

In a still further aspect of the present invention, there is also provided use of the compound of the formula (I) for the manufacture of a medicament.

In a still further aspect of the present invention, there is also provided use of the compound of the formula (I) for the manufacture of a nerve growth promoting agent.

In a still further aspect of the present invention, there is also provided use of the compound of the formula (I) for the manufacture of a preventive and/or therapeutic drug for dementia and/or malignant tumor.

In a still further aspect of the present invention, there is also provided a method for treating cerebral diseases and/or malignant tumors which comprises administering an effective amount of the compound of the formula (I) to a patient in need thereof.

BEST MODE FOR CARRYING OUT THE INVENTION

Figure 1:
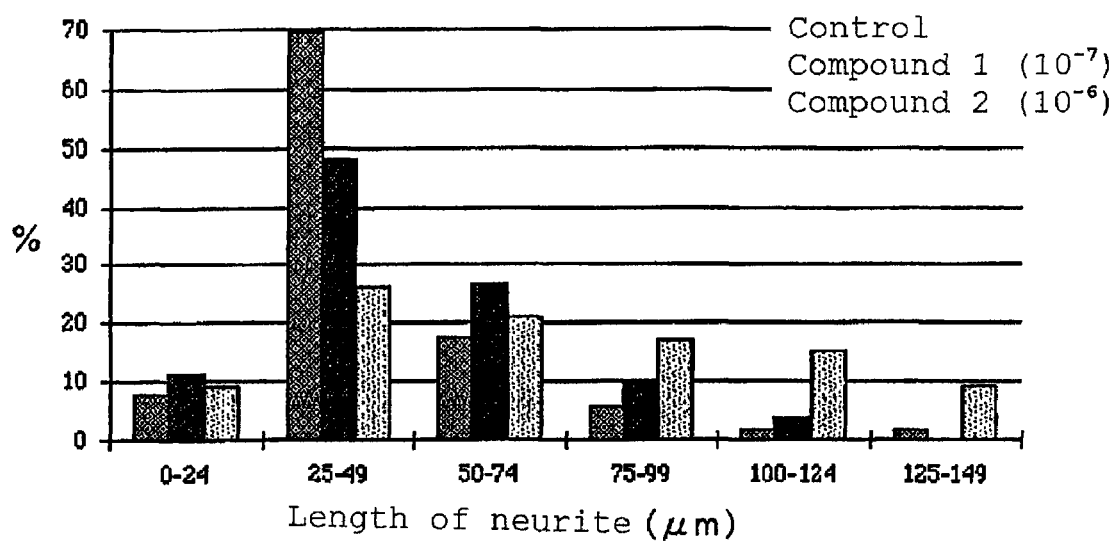
FIG. 1 illustrates the effect of the compounds of the invention on neurite outgrowth.

In the formula (I), $R^1$, $R^2$, $R^3$ and $R^4$ can be any of the above-described groups and are particularly preferably hydrogen atom. n stands for a number from 0 to 20, preferably 2 to 18, more preferably 6 to 16, and particularly preferably 8 to 14.

The compound (I) may be in the form of a hydrate. There are many isomers in the compound (I) and these isomers are also embraced in the present invention.

The invention compound (I) can be prepared, for example, in accordance with the following reaction scheme:

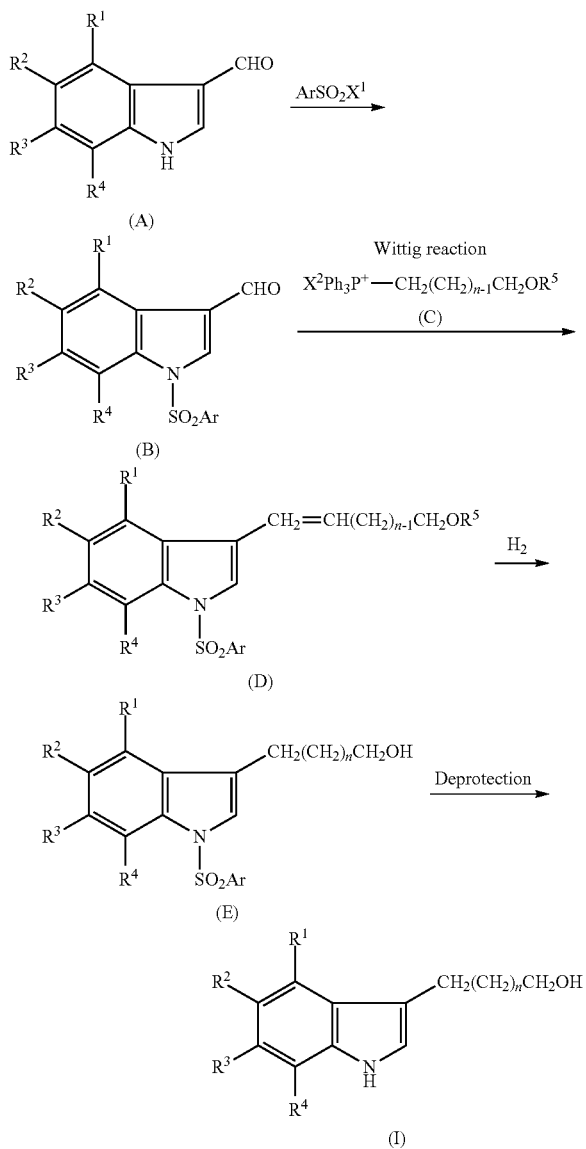

wherein Ar represents an aromatic hydrocarbon group, $X^1$ and $X^2$ each represents a halogen atom, $R^5$ represents a hydroxyl-protecting group and $R^1$, $R^2$, $R^3$, $R^4$ and n have the same meanings as described above.

Specifically, an indole-3-carboxyaldehyde (A) is reacted with an arylsulfonyl halide to give Compound (B), which is in turn reacted with Compound (C) according to Wittig reaction to give Compound (D), and then Compound (D) is halogenated to remove the hydroxyl-protecting group therefrom to give Compound (E), and then the amino-protecting group in the Compound (E) is removed to obtain the compound (I) of the invention.

As the arylsulfonyl halide, p-methoxybenzenesulfonyl chloride can be illustrated. The reaction between the indole-3-carboxyaldehyde (A) and the arylsulfonyl halide is preferably conducted in the presence of an alkali such as sodium hydroxide.

As the hydroxyl-protecting group ($R^5$) in the Compound (C) used in the Wittig reaction, preferred is a group removable by hydrogenation, such as, for example, benzyl group. The Wittig reaction is preferably conducted by reacting Compound (C) with n-butyl lithium, followed by reaction with potassium t-butoxide and then with Compound (B).

Hydrogenation of Compound (D) is preferably conducted by reacting it with hydrogen in the presence of, for example, a palladium catalyst. In the subsequent reaction for eliminating the arylsulfonyl group, an amalgam hydroxide and sodium hydrogenphosphate are preferably used.

Since the resulting compound (I) exhibits an excellent nerve growth promoting effect and potent antioxidative and antitumor effects, and has a molecular weight low enough to pass through the blood-brain barrier, it is useful as a preventive and/or therapeutic drug for cerebral diseases typified by dementia of animals including human being and malignant tumors such as cerebral tumor.

The medicament according to the present invention can be administered either orally or parenterally (such as intramuscular, subcutaneous, intravenous or suppository). In preparing these dosage forms, it is preferred to use a medical composition containing the compound (I) of the invention and a pharmaceutically acceptable carrier. Oral preparations can be formulated into tablets, coated tablets, granules, capsules, solutions, syrups, elixirs, or oily or aqueous suspensions in a manner known per se in the art after adding to the compound (I) an excipient and, if necessary, a binder, a disintegrator, a lubricant, a colorant and/or a corrigent. Examples of the excipient include lactose, corn starch, sucrose, glucose, sorbitol and crystalline cellulose. Examples of the binder include polyvinyl alcohol, polyvinyl ether, ethyl cellulose, methyl cellulose, gum arabic, tragacanth, gelatin, shellac, hydroxypropyl cellulose, hydroxypropyl starch and polyvinyl pyrrolidone. Examples of the disintegrator include starch, agar, gelatin powder, crystalline cellulose, calcium carbonate, sodium bicarbonate, calcium citrate, dextran and pectin; and examples of the lubricant include magnesium stearate, talc, polyethylene glycol, silica and hardened vegetable oil. As the colorant, pharmaceutically acceptable ones can be used. Examples of the corrigent include cocoa powder, menthol, aromatic acid, peppermint oil, camphor and cinnamon powder. The tablets and granules may be applied with sugar coating, gelatin coating or the like as needed.

The dose of the medicine of the invention varies depending on the disease to be treated, administration route, symptoms and weight of a patient. For a human adult, the daily dose of the compound (I) will be usually within a range of from 0.001 to 1000 mg/day, and preferably from 0.1 to 100 mg/day. This daily dose is administered once a day or in 2 to 4 portions a day.

EXAMPLES

The present invention will be hereinafter described in further detail by way of examples. It should however be borne in mind that the present invention is not limited to or by these examples.

Reference Example 1

3-indolecarboxyaldehyde (1.003 g, 6.91 mmol) was dissolved in 20 mL of dry dichloromethane, and then sodium hydroxide (410 mg, 10.24 mmol) was added thereto. After allowing to stand for 15 minutes at room temperature, the resulting mixture was added with 4-methoxybenzenesulfonyl chloride (2.112 g, 10.22 mmol) and was allowed to stand again at room temperature for 12 hours. To the reaction mixture, 100 mL of ammonium chloride was added and the mixture was extracted with 100 mL of ethyl acetate three times. The combined organic layer was washed with saline, dried over anhydrous magnesium sulfate and then concentrated. The residue was recrystallized to give 1-(4-methoxybenzensulfonyl)-3-indolecarboxyaldehyde as pearl-like pink crystals.

Melting point: 138 to 139° C.

$^1$H-NMR (200 MHz): 3.81(s,3H,H-9), 6.94(d,J=9.1 Hz,2H,H-3",5"), 7.32-7.45(m,2H,H-5,6), 7.91(d,J=9.1 Hz,2H,H-2",6"), 7.87-7.96(m,1H,H-4), 8.23(s,1H,H-2), 8.25 (dd,J=6.9 Hz,J=2.7 Hz,1H,H-7), 10.09(s br,1H,H-8).

$^{13}$C-NMR (50 MHz): 55.81(C-9), 113.25(C-7), 114.94(C-3",5"), 122.26(C-3), 122.60(C-4,6), 125.01(C-5), 126.27(C-2",6"), 128.63(C-3'), 129.61(C-7'), 135.23(C-1"), 136.24(C-2), 164.54(C-4"), 185.34(C-8).

Reference Example 2

A solution of 15-benzyloxypentadecyltriphenyl phosphonium bromide (755 mg, 1.14 mmol) dissolved in 10 ml of tetrahydrofuran (THF) was added dropwise to n-butyl lithium (1.5M in hexane, 0.8 mL, 1.20 mmol) at −78° C. in an argon gas atmosphere. After reaction at room temperature for 15 minutes, potassium t-butoxide (131 mg, 1.16 mmol) was added to the reaction mixture at 0° C. The resulting solution was then allowed to stand at room temperature for 15 minutes. After the solution was cooled again to −78° C., a THF solution of 1-(4-methoxybenzenesulfonyl)-3-indolecarboxyaldehyde (307 mg, 0.97 mmol) was slowly added to the solution. The resulting mixture was allowed to stand at −78° C. for 1 hour, and then allowed to stand at 0° C. for 1.5 hours. Ammonium chloride (50 mL) was added to the mixture and the resulting mixture was extracted three times with 60 ml of ethyl ether. The combined organic layer was washed with saline, dried over anhydrous magnesium sulfate and then concentrated. The residue was purified by chromatography on a silica gel column to give 3-(16-benzyloxyhexadecenyl)-1-(4-methoxybenzenesulfonyl)indole as a white solid.

$^1$H-NMR (200 MHz), δ: 1.26(s br,20H,H-12 to H-21), 1.46-1.65(m,4H,H-11,22), 2.32(m,2H,H-10), 3.47(t,J=6.6 Hz,2H,H-23), 3.77(s,3H,H-25), 4.51(s,2H,H-24), 5.82(dt, J=11.1 Hz,J=6.9 Hz,1H,H-9), 6.40(d,J=11.1 Hz,1H,H-8), 6.86(d,J=8.7 Hz,2H,H-3"',5"'), 7.21-7.36(m,7H,H-2'" to H-6'", H-5,6), 7.51(s,1H,H-2), 7.53(d,J=6.9 Hz,1H,H-4), 7.82(d,J=8.7 Hz,2H,H-2",6"), 7.99(d,J=7.6 Hz,1H,H-7).

$^{13}$C-NMR (500 MHz) δ: 26.35(C-10), 29.83(C-11 to C-22), 55.75(C-25), 70.70(C-23), 72.99(C-24), 113.74(C-7), 114.56(C-9), 117.58(C-3",s5"), 119.41(C-3), 119.71(C-5), 123.31(C-4), 123.58(C-6), 124.92(C-2",6"), 127.61(C4"'), 127.74(C-3'",5'"), 128.49(C-2'",6'"), 129.18(C-8), 129.90(C-3'), 131.25(C-7'), 134.79(C-1"), 135.02(C-2), 138.92(C-1"'), 163.92(C-4").

In a similar manner to Reference Examples 1 and 2, 3-(10-benzyloxydecenyl)-1-(4-methoxybenzenesulfonyl)indole (yield: 70%), 3-(12-benzyloxydodecenyl)-1-(4-methoxybenzenesulfonyl)indole (yield: 87%) and 3-(14-benzyloxytetradecenyl)-1-(4-methoxybenzenesulfonyl)indole (yield: 88%) were obtained.

Reference Example 3

3-(16-benzyloxyhexadecenyl)-1-(4-methoxybenzensulfonyl)indole (530 mg, 0.86 mmol) was dissolved in 25 mL of ethanol and added to palladium supported on activated charcoal (5%, 50 mg). The resulting mixture was allowed to stand at room temperature for 3 hours under 1 atmospheric pressure of hydrogen. After filtration, the reaction mixture was extracted with ethyl ether. The organic layer was concentrated under reduced pressure. The residue was purified by flash chromatography to give 3-(16-hydroxyhexadecyl)-1-(4-methoxybenzenesulfonyl)indole as a white solid (417 mg, 92%).

$^1$H-NMR (200 MHz) δ: 1.26(s br,24H,H-10 to H-21), 1.62 (m,4H,H-9,22), 2.63(t,J=7.4 Hz,2H,H-8), 3.64(t,J=6.4 Hz,2H,H-23), 3.77(s,3H,H-24), 6.85(d,J=8.8 Hz,2H,H-3",5"), 7.25(m,2H,H-5,6), 7.29(s,1H,H-2), 7.47(d,J=6.6 Hz,'H, H-4), 7.79(d,J=8.8 Hz,1H,H-2",6"), 7.97(d,J=7.6 Hz,1H,H-7).

$^{13}$C-NMR (50 MHz) δ: 24.93(C-21), 25.80(C-9), 28.94(C-20), 29.70(C-10 to C-19), 32.87(C-8), 55.63(C-24), 63.14(C-23), 113.81(C-7), 114.36(C-9), 119.54(C-3",5"), 122.64(C-4), 122.89(C-6), 123.66(C-3), 124.50(C-5), 128.99(C-2",6"), 129.99(C-3'), 131.31(C-7'), 134.85(C-1"), 135.44(C-2), 163.60(C"-4).

In a similar manner to Reference Example 3, 3-(10-hydroxydecyl)-1-(4-methoxybenzenesulfonyl)indole (yield: 92%), 3-(12-hydroxydodecyl)-1-(4-methoxybenzenesulfonyl)indole (yield: 92%) and 3-(14-hydroxytetradecyl)-1-(4-methoxybenzenesulfonyl)indole (yield: 93%) were obtained.

Example 1

To a solution of 3-(16-hydroxyhexadecyl)-1-(4-methoxybenzenesulfonyl)indole (400 mg, 0.72 mmol) dissolved in 20 ml of dry methanol were added disodium hydrogenphosphate (205 mg, 1.44 mmol) and amalgam chloride (6%, 4 g) at 0° C. under argon gas. After the resulting mixture was allowed to stand at room temperature for 12 hours, 50 mL of ammonium chloride was added thereto. The resulting mixture was extracted three times with 60 ml of ethyl ether. The combined organic layer was washed with saline, dried over anhydrous magnesium sulfate and then concentrated. The residue was purified by chromatography on a silica gel column to give 3-(16-hydroxyhexadecyl)indole (Compound 1) as a white solid (204 mg, 75%).

Melting point: 79 to 80° C.

$^1$H-NMR (200 MHz) δ: 1.27(s br,24H,H-10 to H-21), 1.57 (m,2H,H-22), 1.72(m,2H,H-9), 2.76(t,J=7.6 Hz,2H,H-8), 3.64(t,J=6.4 Hz,2H,H-23), 6.97(s,1H,H-2), 7.15(m,2H,H-5,6), 7.35(d,J=7.6 Hz,1H,H-4), 7.62(d,J=7.6 Hz,1H,H-7), 7.93(s br,1H,H-1)

$^{13}$C-NMR (50 MHz) δ: 25.30(C-21), 25.89(C-9), 29.83(C-10 to C-20), 30.32(C-8), 32.97(C-22), 63.26(C-23, 111.15 (C-7), 117.38(C-3), 119.15(C-4,6), 121.12(C-5), 121.94(C-2), 127.79(C-3'), 136.52(C-7')

IR (KBr): 3416(s br,O—H,N—H), 3049(w,=C—H), 2916, 2849(s,C—H), 1638, 1618(m,C=C), 1474, 1457(m, C—H), 1061(w,C—O), 741(m,C—H)

UV (acetonitrile): λmax: 203 nm (ε18864), 222 nm (ε27571), 281 nm (ε5880)

MS (EI): 357.3 (M$^+$,37), 144.2($C_{10}H_{10}N$,4), 130.3 ($C_9H_8N$,100)

In a similar manner to Example 1, the following compounds were obtained.

3-(2-hydroxyethyl)indole (liquid) (Compound 2)

3-(10-hydroxydecyl)indole (melting point: 55 to 56° C.) (Compound 3)

3-(11-hydroxyundecyl)indole (melting point: 60 to 61° C.) (Compound 4)

3-(12-hydroxydodecyl)indole (melting point: 66 to 67° C.) (Compound 5)

3-(14-hydroxytetradecyl)indole (melting point: 72 to 73° C.) (Compound 6)

Test Example 1

Effect on Neurite Outgrowth and Neuron Survival

This experiment was conducted in accordance with the method of Luu, et al. (C. Girlanda-Junges, F. Keyling-Bilger, G. Schemitt & B. Luu, "Effect of Cyclohexenonic Long Chain Fatty Alcohols on Neurite Outgrowth. Study on Structure-Activity Relationship", Tetrahedron, 54, 7735-77481998)). Fetal rat neurons in primary cultures were treated with Compound 1 at the concentrations of $10^{-6}$ and $10^{-7}$ M, followed by incubation for 3 days. As illustrated in FIG. 1, the proportion of the neurons with neurites of 50 μm or longer was found to be higher in the treated group than in the control group, which clearly shows that Compound 1 has a potent neurite extension effect.

Test Example 2

Preventive Effect on Hemolysis in Human Blood Cells Induced by Free Radicals

Figure 2:
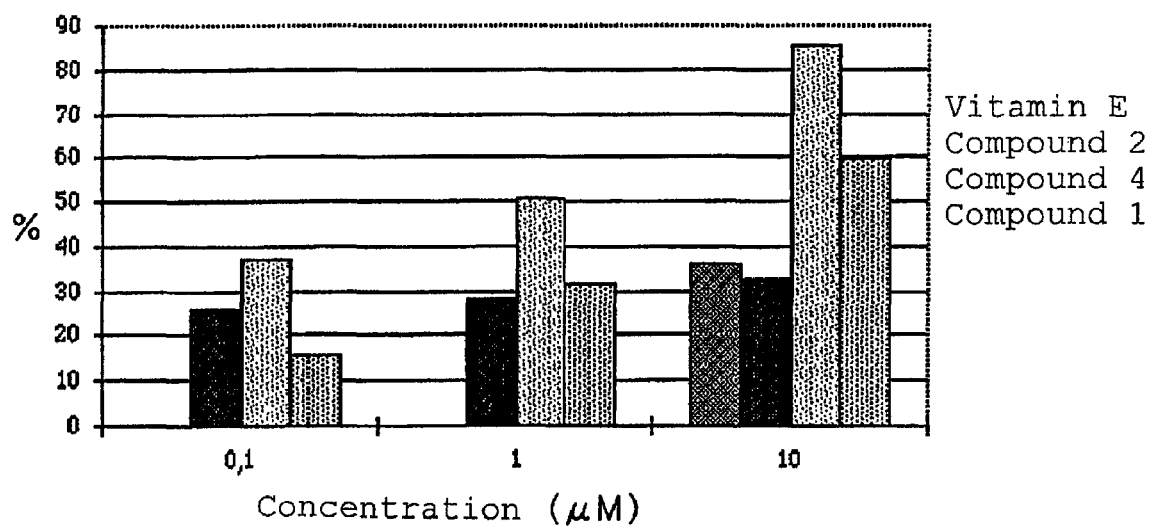
FIG. 2 illustrates the effect of the compounds of the invention on preventing hemolysis of human blood cells induced by free radicals.

An experiment was conducted in accordance with the method of D. Blache. FASEB J. et al. (E. Bourdon, N. Loreau & D. Blache. FABES J. "Glucose and free radicals impair the antioxidant properties of serum albumin", 13, 233-244 (1999)). The time required for 50% hemolysis ($HT_{50}$) was measured and the extension of the time required for $HT_{50}$ compared with that of a control group was plotted on a graph. In this experiment, Vitamin E was employed as a positive control. As illustrated in FIG. 2, the compounds of the invention (Compounds 1, 2 and 4) extended $HT_{50}$, thus exhibiting preventive effect on hemolysis. Particularly, Compound 4 exhibited a strong effect.

Test Example 3

Induction of Differentiation and Apoptosis of Neuroblastoma Cells

Human neuroblastoma cells, Lan-1 (Lan-1: a human neuroblastoma cell line with M1 and M2 muscarinic receptors conjugated with intracellular $Ca^{2+}$) were used to investigate the effects of the present compounds on the induction of proliferation, differentiation and apoptosis. As shown in Table 1, the present compounds (Compounds 1, 3 and 4) exhibited stronger effects on induction of differentiation or apoptosis of neuroblastoma cells rather than on proliferation of the cells.

TABLE 1

| | Concentration μM | Day 1 | | | Day 2 | | | Day 5 | | | Day 7 | | |
|---|---|---|---|---|---|---|---|---|---|---|---|---|---|
| | | Proliferation | Differentiation | Apoptosis | Proliferation | Differentiation | Apoptosis | Proliferation | Differentiation | Apoptosis | Proliferation | Differentiation | Apoptosis |
| Control | | + | − | − | ++ | − | − | ++ | − | +/− | ++ | − | +/− |
| Comp'd 3 | 0.1 | + | + | − | + | + | − | + | − | +/− | ++ | +/− | +/− |
| | 10 | +/− | +++ | − | +/− | ++ | + | +/− | ++ | + | +/− | +++ | + |
| | 100 | − | + | ++ | +/− | + | ++ | +/− | +++ | ++ | | | ++++ |
| Comp'd 4 | 0.1 | ++ | − | − | + | + | − | +/− | +/− | − | ++ | +/− | − |
| | 10 | + | ++ | − | +/− | ++ | + | +/− | ++ | − | +/− | ++ | +/− |
| | 100 | +/− | + | +++ | − | − | +++ | + | ++++ | + | | | ++++ |
| Comp'd 1 | 0.1 | + | +/− | − | ++ | +/− | − | +/− | +/− | − | +/− | + | +/− |
| | 10 | + | ++ | +/− | + | +++ | +/− | +/− | +++ | ++ | +/− | ++++ | ++ |
| | 100 | +/− | +++ | + | − | ++++ | + | − | + | +++ | − | ++ | +++ |

++++: Extremely strongly stimulated (reinforced).
+++: Very strongly stimulated (reinforced).
++: Strongly stimulated (reinforced).
+: Stimulated (reinforced).
+/−: No change.
−: Decreased (weakened).

INDUSTRIAL APPLICABILITY

The present compound (I) has an excellent nerve growth promoting effect, an antioxidative effect and an antitumor effect and is therefore useful as a preventive and/or therapeutic drug for cerebral diseases such as dementia or malignant tumors such as cerebral tumor.

The invention claimed is:

1. A method for treating a cerebral dementia disease comprising:
   administering to a patient in need thereof a therapeutically effective amount of an indole long-chain alcohol, according to the following formula (I):

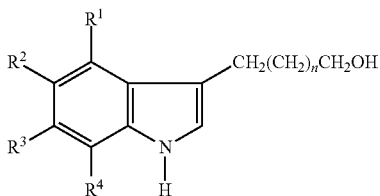
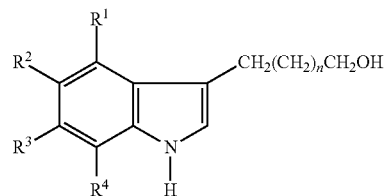

wherein
R$^1$, R$^2$, R$^3$, and R$^4$ each independently represent a hydrogen atom, a methyl group, an acetyl group, or a hydroxyl group, and n represents a number from 0 to 9.

2. The method according to claim 1, wherein n represents a number from 0 to 3.

3. The method according to claim 1, wherein n represents a number from 3 to 5.

4. The method according to claim 1, wherein n represents a number from 5 to 7.

5. The method according to claim 1, wherein n represents a number from 7 to 9.

6. The method according to claim 1, wherein the therapeutically effective amount of the indole long-chain alcohol is from 0.001 to 1000 mg/day.

7. The method according to claim 1, wherein the therapeutically effective amount of the indole long-chain alcohol is administered either once per day or in two to four divided doses per day.

8. The method according to claim 1, wherein the therapeutically effective amount of the indole long-chain alcohol is administered orally or parenterally.

9. A method for treating a malignant brain tumor comprising:
administering to a patient in need thereof a therapeutically effective amount of an indole long-chain alcohol, according to the following formula (I):

wherein R$^1$, R$^2$, R$^3$, and R$^4$ each independently represent a hydrogen atom, a methyl group, an acetyl group, or a hydroxyl group, and n represents a number from 0 to 9.

10. The method according to claim 9, wherein n represents a number from 0 to 3.

11. The method according to claim 9, wherein n represents a number from 3 to 5.

12. The method according to claim 9, wherein n represents a number from 5 to 7.

13. The method according to claim 9, wherein n represents a number from 7 to 9.

14. The method according to claim 9, wherein the therapeutically effective amount of the indole long-chain alcohol is from 0.001 to 1000 mg/day.

15. The method according to claim 9, wherein the therapeutically effective amount of the indole long-chain alcohol is administered either once per day or in two to four divided doses per day.

16. The method according to claim 9, wherein the therapeutically effective amount of the indole long-chain alcohol is administered orally or parenterally.

17. The method according to claim 1, wherein said indole long-chain alcohol is administered in combination with a pharmaceutically acceptable carrier.

18. The method according to claim 9, wherein said indole long-chain alcohol is administered in combination with a pharmaceutically acceptable carrier.

* * * * *